United States Patent
Pfister et al.

(10) Patent No.: US 7,903,856 B2
(45) Date of Patent: Mar. 8, 2011

(54) METHOD FOR POST-PROCESSING A THREE-DIMENSIONAL IMAGE DATA SET OF VESSEL STRUCTURE

(75) Inventors: Marcus Pfister, Bubenreuth (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 840 days.

(21) Appl. No.: 11/901,674

(22) Filed: Sep. 18, 2007

(65) Prior Publication Data

US 2008/0212857 A1  Sep. 4, 2008

(30) Foreign Application Priority Data

Sep. 26, 2006 (DE) .................. 10 2006 045 423

(51) Int. Cl.
*G06K 9/00* (2006.01)

(52) U.S. Cl. ......... 382/128; 382/131; 382/129; 382/130; 382/133; 382/134; 382/294; 382/154; 382/276; 378/4; 378/21; 378/62; 378/901; 600/410; 600/423; 600/427; 345/419; 345/424

(58) Field of Classification Search .................. 382/128, 382/131, 266, 129, 294, 276, 154, 134, 130; 345/419, 424; 372/62, 19; 128/916, 920, 922; 600/410, 423, 427

See application file for complete search history.

(56) References Cited

U.S. PATENT DOCUMENTS

| | | | |
|---|---|---|---|
| 7,574,026 B2 * | 8/2009 | Rasche et al. | 382/128 |
| 7,602,970 B2 * | 10/2009 | Florin et al. | 382/173 |
| 7,715,626 B2 * | 5/2010 | Florin et al. | 382/173 |
| 7,787,683 B2 * | 8/2010 | Khamene et al. | 382/130 |
| 7,822,254 B2 * | 10/2010 | Yatziv et al. | 382/131 |
| 2006/0188139 A1 | 8/2006 | Khamene et al. | |

FOREIGN PATENT DOCUMENTS

WO  WO 2004/072903 A2  8/2004

* cited by examiner

*Primary Examiner* — Wesley Tucker
*Assistant Examiner* — Nancy Bitar

(57) ABSTRACT

The invention relates to a method for post-processing a 3D image data set of a vessel structure of a human or animal body, in which a 2D DSA (Digital Subtraction Angiography) of the vessel structure is recorded and registered with the 3D image data set. The 2D DSA is compared with a corresponding projection image computed from the 3D data set and this is changed, e.g. by changing the segmentation parameters, to adapt it to the 2D DSA. This enables the outstanding local resolution of the 2D DSA to be used for improving the 3D image data set.

14 Claims, 4 Drawing Sheets

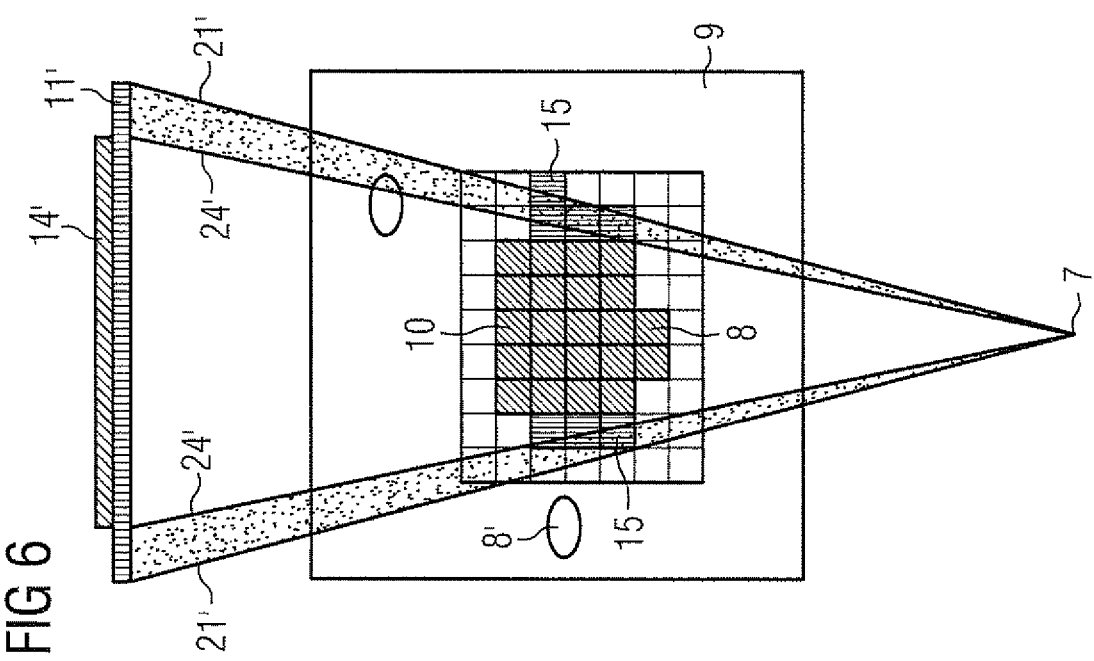
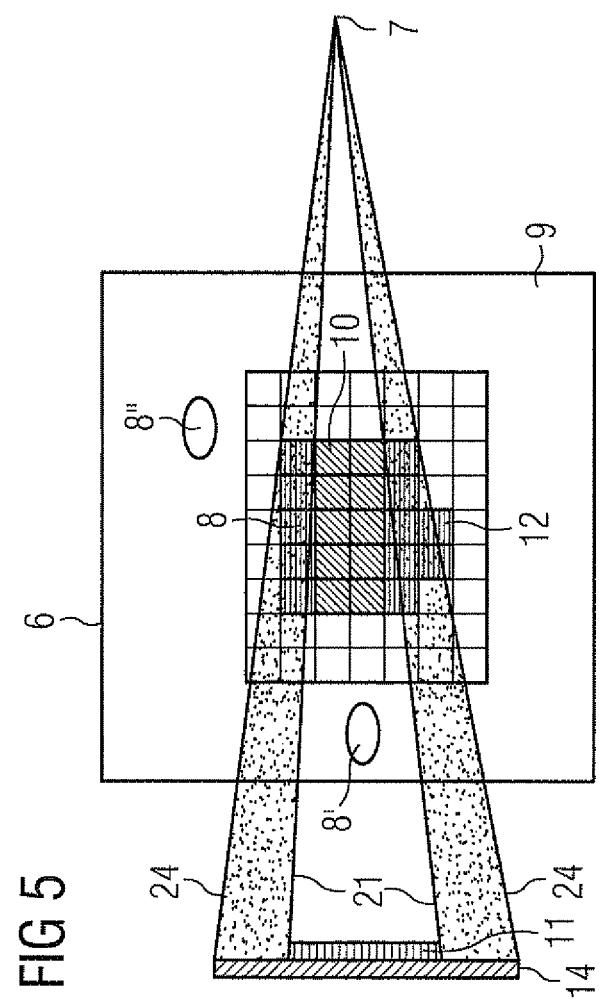

METHOD FOR POST-PROCESSING A THREE-DIMENSIONAL IMAGE DATA SET OF VESSEL STRUCTURE

CROSS REFERENCE TO RELATED APPLICATIONS

This application claims priority of German application No. 10 2006 045 423.5 filed Sep. 26, 2006, which is incorporated by reference herein in its entirety.

FIELD OF THE INVENTION

The invention relates to a method for post-processing a three-dimensional (3D) image data set of a vessel structure of the body of a human or an animal, with the three-dimensional image data set having been recorded with a medical imaging modality.

BACKGROUND OF THE INVENTION

To show blood vessels there are currently recording options available with which three-dimensional image data records can be created. Imaging modalities can be used for this purpose, e.g. computer tomography (CT), magnetic resonance tomography (MR) or 3D rotation angiography.

Important applications in such case are the diagnosis of vessel diseases such as aneurysms and stenoses and the planning of therapies. The planning is a matter of predicting the probability of a rupture of aneurysms and of selecting the therapy depending on this prediction or the selection of suitable therapeutic systems (e.g. stents) and their dimensions (e.g. diameter and length). Specifically in the assessment of rupture probability of aneurysms a three-dimensional image data set of the vessel structure can be used as the basis for a computer simulation (using "Computational Fluid Dynamics"), with which the probability of a rupture can be computed. An important variable here is for example the diameter of the neck of an aneurysm. The exact assessment of the aneurysm neck can under some circumstances influence the decision as to whether the latter is to be removed by a clinical intervention or whether what is referred to intravascular coiling is to be performed instead.

It is thus very important, as a basis for therapy planning, to have as exact as possible a three-dimensional image of the vessel, especially in the area surrounding the diseased vessel.

The three-dimensional image data sets generated with currently used imaging modalities do not however possess any high local resolution. With MR the signal-to-noise ratio is the limiting factor which restricts the resolution of the MR image to around 1 mm$^3$. An x-ray image does in principle have a high local resolution; however a large part of local resolution is lost through the reconstruction of many x-ray images into one three-dimensional image data set, e.g. in CT or in 3D rotation angiography. To minimize the x-ray dose for the patient no resolutions of significantly more than 0.2 to 1 mm$^3$ can be thus be achieved even with this method.

Furthermore three-dimensional image data sets are segmented as a rule after recording and reconstruction, with the data set being divided up into segments, i.e. volume areas, which are each assigned to the vessel structure or to the background. The image intensity of the background is set to zero. This is used to show the vessels without surrounding tissue and bone.

In the area of the neck of an aneurysm in particular it is very difficult to perform a segmentation correctly. Once again the lack of local resolution in the reconstructed 3D image data set as well as reconstruction artifacts are responsible for this. If the segmentation is thus optimized to a specific area (e.g. the aneurysm neck), under some circumstances this leads to a less than optimum segmentation of other areas (e.g. feeding vessels, middle of the aneurysm).

What is referred to as Digital Subtraction Angiography (DSA) is also known for showing vessels. In this case two chronologically consecutive images of the vessel structure are recorded, usually with a C-arm x-ray device. A contrast medium is injected into the bloodstream between the images. The two x-ray images thus only differ in the depiction of the vessels which are hardly visible in the first image (mask image) but which are strongly contrasted in the second image (filling image) however. The digitized images are subtracted from one another. Thus only the contrasted blood vessels are to be seen in the difference image, the DSA. The DSA thus delivers two-dimensional (2D) images with a high local resolution, but without depth information. Thus the DSA is also referred to below as the "2D DSA".

WO 2004/072903 A2 discloses a method to creating a 3D model of a vessel structure, which also uses a reconstructed three-dimensional image and 2D projection images. In this patent the center lines of the vessels are first selected on the 3D image and then automatically segmented. These center lines are projected onto the 2D projection images and the outlines of the vessel structure on the 2D projection images is determined and projected back into the 3D image.

SUMMARY OF THE INVENTION

The invention has set itself the task of making available a method for post-processing of a 3D image data set of a vessel structure which does not require any model computation and thus no intervention by a user.

To do this the invention provides a method in accordance with the claims.

The 3D image data set can originate from a CT or MR, but also be produced by 3D rotation angiography in a rotation pass on the same angiography system with which the 2D DSA was also produced. The method can either be executed while the patient is supported in the angiography system, e.g. a C-arm x-ray device, or can occur later as post-processing. The 3D image data set can for example be obtained by two rotation passes of a C-arm x-ray device subtracted from each other, in which the second pass (filling pass) is contrasted. The first pass without contrast (mask pass) will be subtracted from these passes, and the series of images reconstructed into a three-dimensional presentation of the vessel structure.

Preferably a first working projection direction which is as good as possible will then be selected on the 3D image data set, in which for example the aneurysm is shown as free of overlays as possible. A number of projection directions can also be selected simultaneously, as explained in greater detail below. Preferably in this case projection directions which cannot be set because of the geometry of the C-arm are automatically forbidden.

A 2D DSA of the vessel structure in the selected first direction of projection is then provided, e.g. with a C-arm system, possibly also with a biplane system. In the special case in which the 3D image data set has been reconstructed from two rotation passes of a C-arm x-ray system subtracted from one another, these 2D DSAs are already contained in the rotation passes. Preferably only these angulations already present are able to be set or displayed.

Subsequently the 3D image data set and the 2D DSA are segmented. This means that they are divided up into volume areas or image areas which are assigned to either the vessel structure or the background. Such volume or image areas can have any form and will be referred to below as "segments". The segmentation is undertaken by a threshold value method, i.e. all pixels or voxels lying above the threshold value are either set to a common, high value or are left unchanged, whereas all pixels or voxels lying below the threshold value are set to zero. This also serves to represent the vessels without the surrounding tissue and bone. The threshold value is automatically or manually adapted for this purpose and is constant for an image data set in each case (global threshold value) Alternatively the segmentation can also be undertaken using a transfer function.

The 2D DSA is subsequently registered with the 3D image data set. This means that the respective coordinate systems of the two image sets are related to each other by a transformation matrix for example, so that, from the position of a voxel in the 3D image data, the position of the pixel corresponding to this point in space can be determined on the 2D DSA. Conversely the function is not unique, since a beam of voxels through the 3D image data set belongs to each pixel of the 2D DSA.

The registration can either be achieved by the so-called 2D-3D registration method in which for example different projections are calculated from the 3D image data set and compared to the 2D DSA. In the special case in which the 3D image data set was obtained with the same angiography systems as the 2D DSA, the registration can be determined more easily from the known system geometry.

Subsequently in step (e) a projection of the 3D image data set onto an image plane in the selected first projection direction is calculated and thus a calculated projection image created. This is compared in step (f) with the 2D DSA and adapted to the latter by changing the 3D image data set. This means that the 3D image data set is thus post processed, which will be explained in greater detail below. Expressed in simple terms a 2D DSA is "overlaid" with the corresponding computed projection image and deviations from the 2D DSA are detected and if necessary corrected.

Optionally the 3D image data set can be scaled up before step (f) to a higher local resolution, so that the more precise location information of the 2D DSA is not lost in the unsharp pixels of the 3D image data set.

Preferably the steps (c) to (f) are repeated with a second 2D DSA of the vessel structure which are recorded from a second direction of projection. This second direction of projection preferably lies at an angle of around between 30° and 110°, especially preferably 80° to 100° to the first direction of projection. Mostly it is preferably an angle of around 90°. This allows the 3D image data set to be adapted to high-resolution 2D DSAs from different directions of view.

In accordance with an especially preferred embodiment, a number of 2D DSAs of the vessel structure, e.g. 3 to 5, are provided in a number of projection directions and steps (c) to (f) with these number of 2D DSAs and the corresponding projection directions through the 3D image data set repeated. The 3D image data set is iteratively changed and improved in this way.

The step (f) of comparison and automatic change is executed as described in the claims.

Step (f2) is therefore necessary, since the 3D position of the vessel to be adapted must be obtained by referring back to the 2D projection onto the computed projection image. It is thus sensible to select a direction of projection in which the vessel structure is shown as free of overlays as possible. In addition the system geometry must be known. If the projection of a vessel section is then traced back on the basis of the system geometry to the x-ray focus, only one vessel can lie on this path, of which the 3D position is then known. Preferably this method is used for determining the 3D position of the differing segment areas in the volume of the 3D image data set.

If the 3D position of the differing vessel section in the 3D image data set is then known the segmentation threshold values for the 3D image data set can be changed so that the differences are reduced. In this case the segment boundaries between the vessel section and the background are shifted through pixel-by-pixel changing of a segmentation threshold value of the 3D image data set. This means that the segmentation parameters of the 3D image data set are adapted locally (not globally) to guarantee an optimum 3D display. Optionally the voxel-by-voxel segmentation threshold values can be smoothed to avoid abrupt transitions.

Especially preferably the method is used for a cerebral vessel structure.

BRIEF DESCRIPTION OF THE DRAWINGS

The invention will now explained in greater detail on the basis of exemplary embodiments with reference to the enclosed drawings. In the drawings:

FIG. 5 shows a schematic display of the 3D image data set with a computed projection and 2D DSA in a first direction of projection;

FIG. 6 shows the schematic display of the 3D image data set of FIG. 5 with a computed projection and a 2D DSA in a second projection direction;

DETAILED DESCRIPTION OF THE INVENTION

Figure 1:
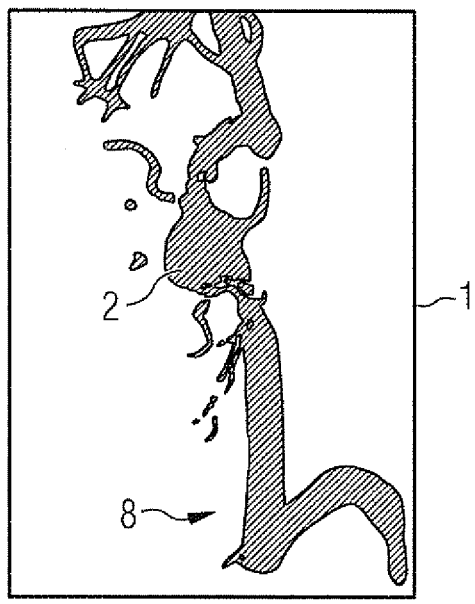
FIG. 1 shows a typical display of a 2D DSA of a vessel structure.

FIG. 1 shows a typical 2D DSA 1 of a vessel structure 2 with an aneurysm 2a. As one might suspect, the 2D DSA has outstanding local resolution but there is an absence of any depth information.

Figure 2:
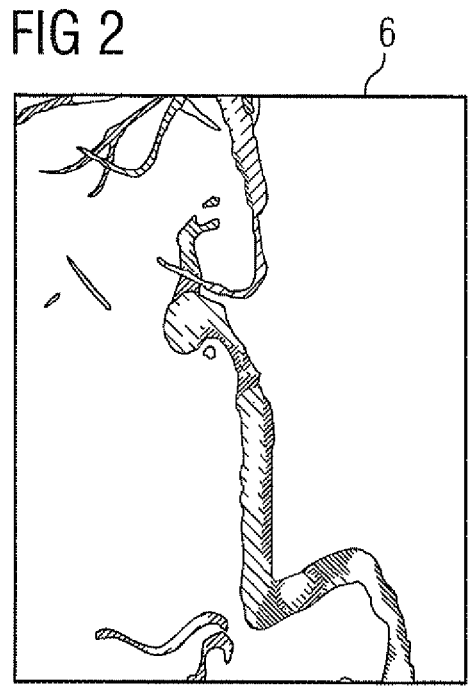
FIG. 2 shows a diagram of a 3D image data set of the same vessel structure in a "volume rendering" presentation

FIG. 2 on the other hand shows a three-dimensional display 3 of the same vessel tree which has been obtained by a 3D rotation pass with a C-arm x-ray device. The 3D image data set has been segmented with a global segmentation threshold value and only the values lying above the threshold value are shown. A so-called "volume rendering" display has been selected in which the vessel structure in the 3D volume has been provided with computed shadow and light effects in order to create a visual three-dimensional impression.

It is precisely with 3D image data sets that the selected global segmentation threshold value is very important, since an aneurysm in particular is displayed markedly differently with different threshold values.

Figure 3:
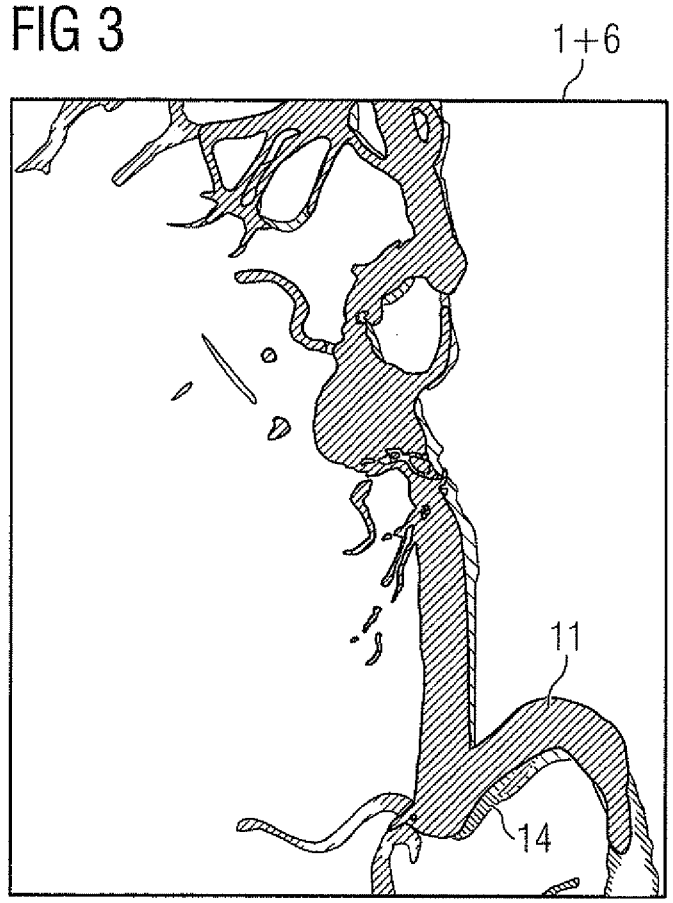
FIG. 3 shows an overlaying of the 2D DSA of FIG. 1 with a projection image computed from the 3D image data set of FIG. 2.

In accordance with the invention, as in FIG. 3, a projection is computed from the 3D image data in the same projection direction in which the 2D DSA was taken. Such a computed projection image is shown as light gray in FIG. 3 and overlaid with the DSA 1 of FIG. 1 (shown in black). As can be seen from FIG. 3 the projection of the image structure 11 on the 2D DSA 1 and the presentation of the vessel structure 14 on the computed projection image 4 do not cover each other exactly, but instead there are discrepancies present. These discrepancies are used with the method for post-processing and improving the 3D image data set described below, since it is assumed that in cases of doubt the 2D DSA delivers more accurate results.

Figure 4:
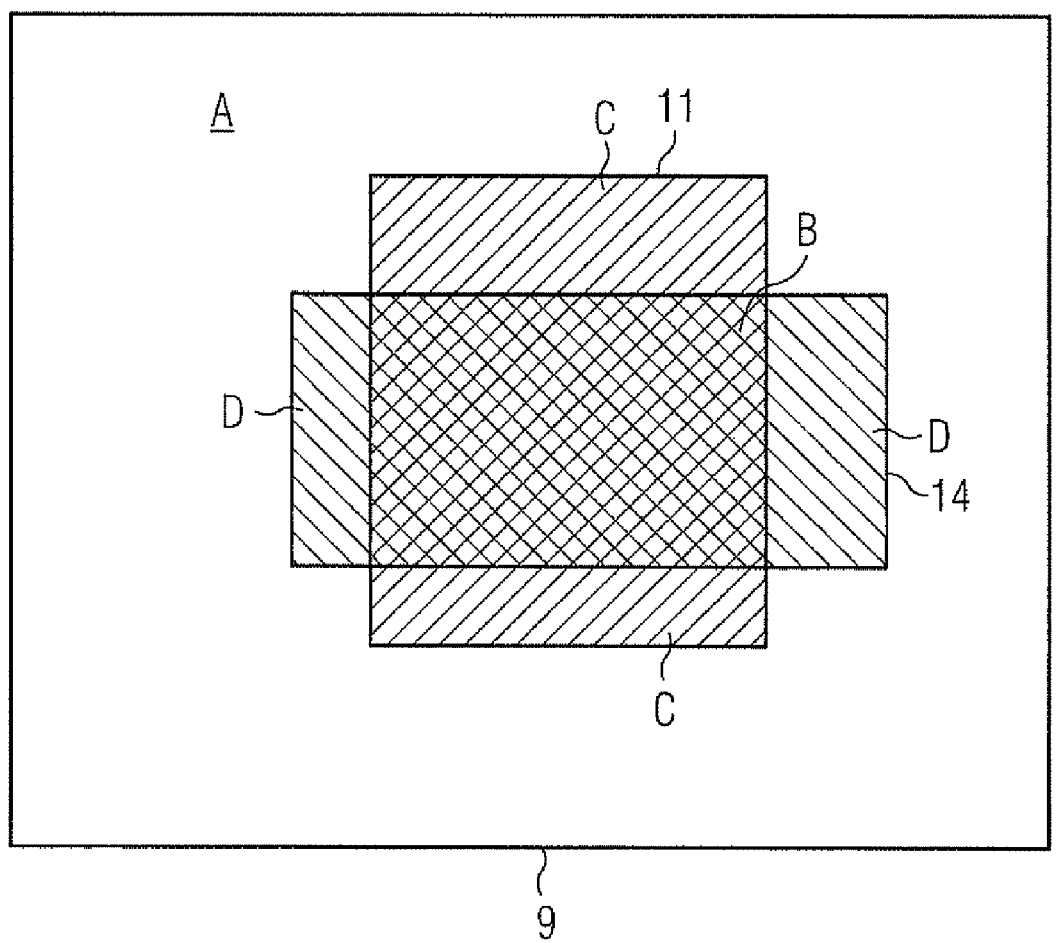
FIG. 4 shows a schematic pixel-by-pixel display of the overlay depicted in FIG. 3.

FIG. 4 shows a schematic diagram of a fictitious section from FIG. 3. The box labeled 11 is intended to represent the pixels of a vessel section on the 2D DSA whereas the box 14 represents a vessel section in the computed projection image. The bold lines in each case depict the segment boundaries between background 9 and the vessel sections 11 or 14. As can be seen the vessel sections 11 and 14 only partly overlap. In sections A and B there is no deviation between the two representations, since either background lies on background or foreground on foreground. In the areas labeled C on the other hand the vessel on the DSA 11 is wider than the calculated projection 14 of the 3D image data set. The corresponding segment boundary of the vessel section 14 is thus to be shifted. This can for example be done by the local threshold value for the pixels in the area being reduced in area C so that the presentation of the vessel section 14 at least partly covers the vessel section 11 in this area.

In the sections D the vessel section 14 in the 3D image data set is too wide in relation to the DSA, the local threshold value in the areas D is thus too small. If the threshold value is increased, the segment boundaries move right and left in the vessel section 14 in the direction of the segment boundaries of the vessel section 11. In this way the vessel presentation 14 in the 3D image data set can be moved into a closer match with the vessel presentation 11 on the 2D DSA1.

An exemplary embodiment is now explained in greater detail with reference to FIGS. 5 and 6. In this exemplary embodiment the segment boundaries are shifted by the voxel-by-voxel adaptation of segmentation threshold values. Thus a global threshold value for segmentation of the 3D image data set is not used but rather a separate threshold value for each voxel, which is iteratively adapted until the 3D image data is adapted to the 2D DSAs.

FIG. 5 shows a schematic cross section through such a 3D image data set 6. The individual voxels are once again shown as small boxes.

The voxels 10 shaded from bottom left to top right and the diagonally shaded voxels 12 represent the voxels which were assigned after segmentation to a specific vessel section 8 within the 3D image data set. Further smaller vessels are labeled 8' and 8". 7 designates the x-ray focus from which the projection cones 21 and 24 originate. The projection cone 24 is the projection of the vessel 8 in the 3D image data set. Projected onto the image plane 14 this produces a two-dimensional display of the vessel 8 on the computed projection image 14. This computed projection image is overlaid with a 2D DSA 11. On this the display of the vessel section in this direction of projection is clearly narrower. Thus if the vessel section 11 is followed back with reference to associated projection beams 21 to the x-ray focus 7, only a smaller part of the vessel section 8 is covered by this. The voxels with vertical-line shading 12 are thus assigned to the vessel section in the 3D image data set, but not however in accordance with the 2D DSA. The threshold value should thus be increased locally in the voxel 12 to bring about a closer match between the two.

This method will preferably be repeated from a second direction of projection, such as that shown in FIG. 6. Here the same vessel 8 is shown in the 3D image data set. A projection of the voxels 10 covered by this in the second direction of projection from the x-ray focus 7 on the image plane 14 thus produces a further computed projection image 14'. The projection cone belonging to this (the path of the x-ray beams) is labeled 24'.

Also recorded in this direction of projection is a 2D DSA 1'. As can be seen in the drawing, the vessel is wider on this 2D DSA than in the computed direction of projection 14'. If the x-ray projection is followed along the rays 21' back to the x-ray focus 7, a transverse shaded voxel 15 is encountered which in accordance with the 2D DSA should belong to the vessel. The local threshold value must thus be reduced for this voxel 15.

More precisely the method can execute iteratively as follows:

A DSA 11 and a computed projection 14 are compared with each other and the voxels 12 or 15 determined, for which the threshold value is to be locally increased or reduced. The threshold value is then increased or reduced by a value, which for example is determined according to the number of differing voxels, or is taken from a predetermined table.

Optionally the threshold values are spatially smoothed thereafter, to avoid abrupt transitions.

Thereafter a new projection of the segmented 3D image data set is computed with the changed threshold values. This new computed projection image is again overlaid with the same or with a second 2D DSA and compared. Then the local threshold value is again increased or reduced in the differing pixels. Optionally the local threshold values are spatially smoothed.

These steps are repeated until a maximum match between computed projection image and DSA is reached, or until one or more local threshold values deviate so widely from the original threshold value that no further improvement is to be expected.

Figure 7:
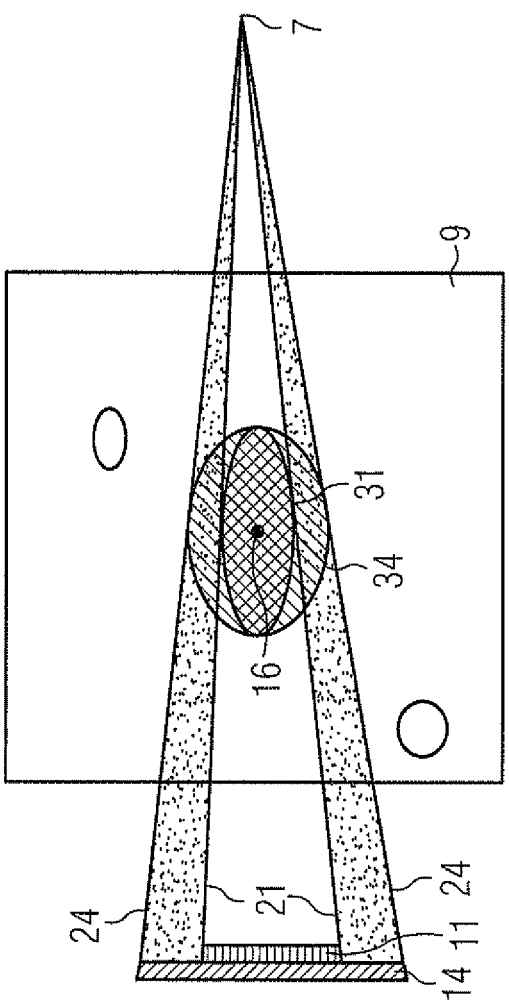
FIG. 7 shows a schematic display of a vessel tree model with a computed projection and a 2D DSA in a first direction of projection.

A non-claimed embodiment will now be explained in greater detail with reference to FIGS. 7 and 8. FIG. 7 shows a section through a vessel tree model which has been computed from the 3D image data set 6 of FIGS. 5 and 6. In the area shown the vessel tree model includes the center line 16 of a vessel, as well as the elliptical diameter of this vessel 34. The cross-section of the vessel is thus defined by this in the vessel tree model and represented by the surface shaded from bottom left to top right.

A projection image 14 is computed from the vessel tree model, in a similar manner to the first exemplary embodiment, with reference to the known system geometry, in that the outlines of the vessel tree model 34 are projected starting from the x-ray focus 7 along the rays 24 onto the image plane 14. This image is compared with a 2D DSA 11. The outlines of the vessel on the 2D DSA are conversely traced back along the rays 21 to the x-ray focus 7. It is evident here that the diameter of the vessel in the direction transverse to the rays 21 on the 2D DSA is narrower than the vessel tree model 34. Accordingly a new ellipse diameter is computed in this direction and the vessel tree model is adapted accordingly. The adapted model 31 is shaded from top left to bottom right.

Figure 8:
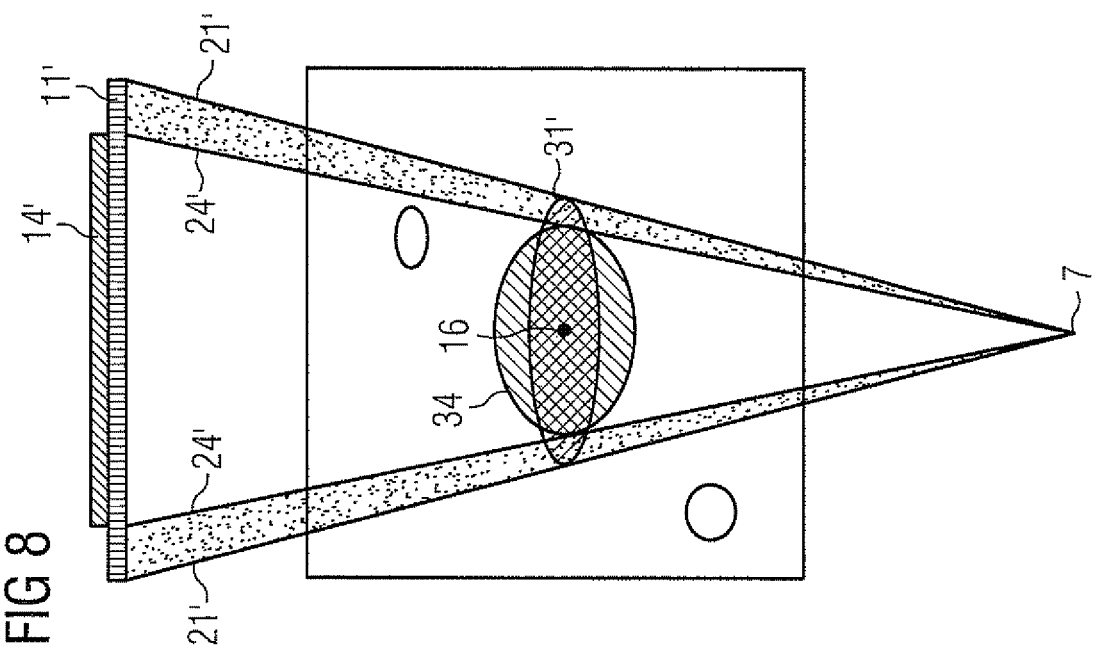
FIG. 8 shows a schematic display of the vessel tree model of FIG. 7 with a computed projection and a 2D DSA in a second direction of projection.

This adaptation can be repeated in accordance with FIG. 8 in a second direction of projection, which is roughly at right angles to the first direction of projection. Here a projection is now computed along the rays 24' of the vessel defined by the center lines 16 and the ellipse 34 onto the image plane 14'. This computed projection image 14' is compared with a 2D DSA 11' which was recorded in the same direction of projection. On the basis of the rays 21' to the x-ray focus 7 the vessel 34 is determined which corresponds in the vessel tree model to the vessel section 11' of the 2D DSA. In this case it is established that this vessel section on the 2D DSA 11' is wider than on the computed projection image 14'. The diameter of the ellipse is thus widened out in this direction, in order to obtain the new vessel tree model 31'.

Although this is not shown in the Figures, the center line 16 could also be shifted to adapt the vessel tree model if this is necessary.

The invention claimed is:

1. A method for post-processing a 3D image data set of a vessel structure of a live body, comprising:
    recording a 2D digital subtraction angiography of the vessel structure in a first direction of projection;
    segmenting the 3D image data set and the 2D digital subtraction angiography through a threshold value method with the segments being assigned to the vessel structure;
    registering the 2D digital subtraction angiography with the 3D image data set;
    generating a computed projection image by computing a projection of the 3D image data set on an image plane in the first direction of projection;
    comparing the computed projection image with the 2D digital subtraction angiography;
    and automatically modifying a local segmentation threshold value of the 3D image data set for adapting the computed projection image to the 2D digital subtraction angiography;
    comparing the segments on the computed projection image and on the 2D digital subtraction angiography to detect a difference area,
    assigning the different segment area into a vessel section in the 3D image data set by back projecting the computed projection image, and
    changing the local segmentation threshold value of the 3D image data set in the different segment area voxel-by-voxel so that a segment assigned to the vessel section on a further computed projection image closely matches a segment assigned to the vessel section on the 2D digital subtraction angiography.

2. The method as claimed in claim 1, wherein the local segmentation threshold value is spatially smoothed changed voxel-by-voxel before computing the further computed projection image.

3. The method as claimed in claim 1, wherein the local segmentation threshold value is changed voxel-by-voxel so that a segment boundary between the vessel section and a background shifts.

4. The method as claimed in claim 1, wherein a second 2D digital subtraction angiography of the vessel structure is recorded in a second direction of projection.

5. The method as claimed in claim 4, wherein the steps of segmenting, registering, generating, comparing, and modifying are repeated with the second 2D digital subtraction angiography on the second direction of projection.

6. The method as claimed in claim 4, wherein the second direction of projection is at an angle of 30° to 110° to the first direction of projection.

7. The method as claimed in claim 1, wherein a plurality of 2D digital subtraction angiographys of the vessel structure are recorded in a plurality of projection directions.

8. The method as claimed in claim 7, wherein the steps of segmenting, registering, generating, comparing, and modifying are repeated with the plurality of 2D digital subtraction angiographys on the corresponding plurality of projection directions.

9. The method as claimed in claim 1, wherein the vessel structure is a cerebral vessel structure.

10. The method as claimed in claim 1, wherein the 2D digital subtraction angiographys is recorded by a C-arm x-ray device.

11. The method as claimed in claim 1, wherein the 3D image data set is recorded by magnetic resonance tomography or computer tomography.

12. The method as claimed in claim 1, wherein the 3D image data set is recorded by 3D rotation angiography and the 2D digital subtraction angiographys is at least partly recorded during the recording of the 3D rotation angiography.

13. The method as claimed in claim 1, wherein the segments are assigned to a background of the 3D image data set.

14. A medical system for post-processing a 3D image data set of a vessel structure of a live body, comprising:
    a computing device that:
    segments the 3D image data set and a 2D digital subtraction angiography of the vessel structure in a first direction of projection through a threshold value method with the segments being assigned to the vessel structure,
    registers the 2D digital subtraction angiography with the 3D image data set,
    generates a computed projection image by computing a projection of the 3D image data set on an image plane in the first direction of projection
    compares the computed projection image with the 2D digital subtraction angiography, and automatically modifies a local segmentation threshold value of the 3D image data set for adapting the computed projection image to the 2D digital subtraction angiography;
    comparing the segments on the computed projection image and on the 2D digital subtraction angiography to detect a difference area,
    assigning the different segment area into a vessel section in the 3D image data set by back projecting the computed projection image, and
    changing the local segmentation threshold value of the 3D image data set in the different segment area voxel-by-voxel so that a segment assigned to the vessel section on a further computed projection image closely matches a segment assigned to the vessel section on the 2D digital subtraction angiography.

* * * * *